United States Patent

Hang-Fu

[11] Patent Number: 5,545,221
[45] Date of Patent: Aug. 13, 1996

[54] APPARATUS AND METHOD FOR IMPLANT PROSTHESES

[76] Inventor: Lee Hang-Fu, 753 Firestone Dr., Avon Lake, Ohio 44012

[21] Appl. No.: 266,601

[22] Filed: Jun. 27, 1994

Related U.S. Application Data

[63] Continuation-in-part of Ser. No. 5,637, Jan. 19, 1993, abandoned.

[51] Int. Cl.$^6$ ................................. A61F 2/12; A61F 2/02
[52] U.S. Cl. ................................................ 623/11; 623/8
[58] Field of Search ........................... 623/8, 7, 17, 11, 623/4, 66

[56] References Cited

U.S. PATENT DOCUMENTS

| | | |
|---|---|---|
| 4,610,690 | 9/1986 | Tiffany . |
| 4,731,081 | 3/1988 | Tiffany et al. . |
| 4,995,882 | 2/1991 | Destoret et al. ........................... 623/8 |
| 5,067,965 | 11/1991 | Ersek et al. . |
| 5,133,753 | 7/1992 | Bark et al. ................................. 623/8 |
| 5,376,117 | 12/1994 | Pinchuk et al. ........................... 623/8 |

OTHER PUBLICATIONS

Bircoll, Autologus Fat Transplantation Employing Liposuction Techniques, Annals of Plastic Surgery, vol. 18, No. 4, pp. 327–329 (1987).
Cosmetic Breast Augmentation Utilizing Antologous Fat & Liposuction Techniques, Mel Bircoll, M. D.
Autologous Fat Transplantation Employing Liposuction Techniques, Mel Bircoll, M. D. & Brian H. Novack, M. D.
Plastic & Reconstructive Surgery, Oct. 1987.
Plastic & Reconstructive Surgery, Dec. 1987.
The Medical Journal of Australia, vol. 148, May 16, 1988.
The Medical Journal of Australia, vol. 149, Sep. 5, 1988.
Plastic & Reconstructive Surgery, 1988.

Primary Examiner—Debra S. Brittingham
Attorney, Agent, or Firm—Oldham & Oldham Co., LPA

[57] ABSTRACT

An implant prosthesis comprising human adipose tissue, preferably of autologous origin, contained within an impermeable or semi-permeable membrane capable of implantation during reconstructive or elective surgery such as mammoplasty.

19 Claims, 1 Drawing Sheet

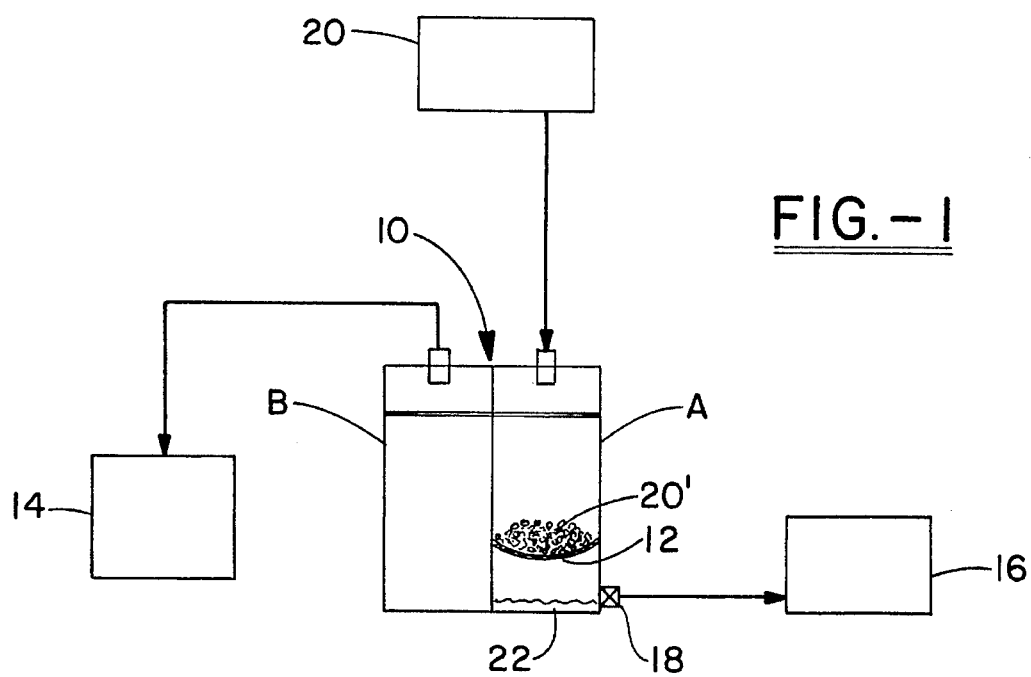
FIG.-1
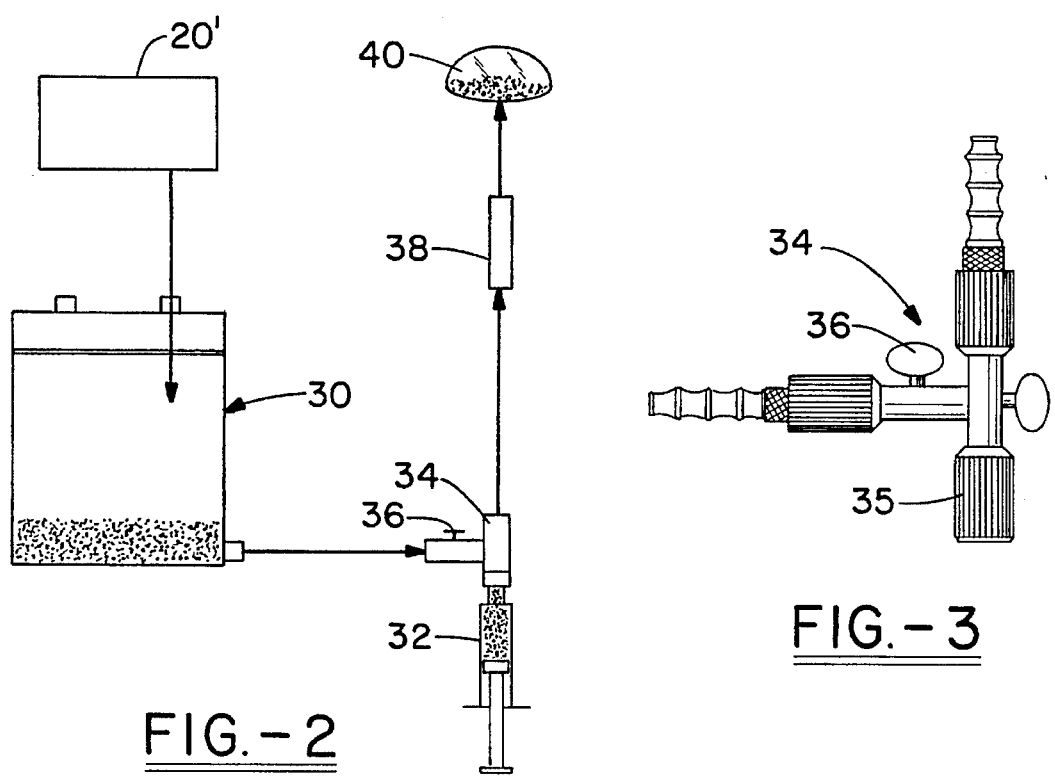
FIG.-2
FIG.-3
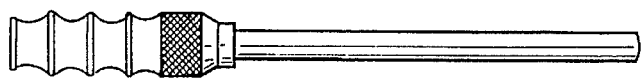
FIG.-4

APPARATUS AND METHOD FOR IMPLANT PROSTHESES

This is a continuation-in-part of application Ser. No. 08/005,637 filed on Jan. 19, 1993, now abandoned.

FIELD OF THE INVENTION

The present invention relates generally to the process of surgical tissue recontouring using implantable prosthesis. More specifically, the present invention relates to a prosthesis comprising human adipose tissue, preferably of autologous origin, contained within an impermeable or semipermeable membrane capable of implantation during reconstructive or elective surgery such as mammoplasty.

BACKGROUND OF THE INVENTION

The use of implantable prosthesis for human body recontouring, for use primarily in the area of breast reconstruction following traumatic or surgical loss of breast tissue or, electively to augment a condition of developmental hypoplasia has been documented for over 80 years. Typically, the prosthesis or implant consists of a flexible envelope containing a liquid or gelatinous material. The envelope is commonly made from silicone, polyurethane or other biocompatible polymers with varying degrees of elastic memory and permeability. Prior art implants have been filled with a variety of materials such as foam rubber, saline and silicone oil or gel.

For many years, silicone filled implants were held out as the clinically accepted standard and superior to other known filling agents, silicone being an inert substance and a natural lubricant. However, silicone filled implants have come under recent criticism by governmental regulatory agencies, members of the medical community and the public at large due to widespread reports of chronic adverse effects such as inflammation, calcification, allergic reactions and even more serious complications resulting from either traumatic rupture of the envelope or the migration of silicone through the envelope membrane or valve into the surrounding tissue and even into the bloodstream. The human body is incapable of eliminating the silicone, thereby requiring the surgical removal of the silicone and treatment of the resulting complications or disease states. Another disadvantage of silicone filled implants is that silicone is radiopaque or radiodense, causing significant obstruction and interference with radiology procedures.

Saline filled implants have for some time been considered a viable alternative to silicone implants and have recently, by default, become the implant/fillant of choice. Implants filled with physiological saline (0.9%) are isotonic and bio-compatible with the fluids of the human body. Therefore, the human body possesses the ability to eliminate the saline which may leak from the implant. In the case of traumatic rupture of the implant, the liberated contents would be essentially non-toxic and non-life threatening to the patient. Saline implants also have the advantage of being radiolucent, but are less desirable than silicone because of saline's low viscosity. Additionally, saline is inherently a poor lubricant and as a result, envelopes of saline filled implants appear to rupture more quickly because of the friction caused when an envelope rubs against itself.

Procedures describing the use of free fat in breast augmentation have also been documented. In these procedures, autologous fat, obtained through liposuction, is aseptically collected and, thereafter, drawn into a syringe for subsequent transcutaneous injection. The fat is injected into multiple areas of the breast in small quantities. However, these procedures appear controversial. Incidences of fat necrosis producing localized inflammation and tumor-like masses, as well as the production of calcifications or nodules formed from the complexing of fatty acids with calcium in tissue fluid have been recorded.

In light of the deficiencies in the prior art, applicant's invention is herein disclosed. Drawings have been provided to illustrate, method for extracting and collecting the fat tissue and subsequently introducing a predetermined volume of fat into a flexible envelope.

SUMMARY OF THE INVENTION

In accordance with the present invention, many of the deficiencies noted with respect to both silicone and saline implants are solved by the use of human adipose tissue as a fillant in a silicone envelope, the adipose tissue, preferably being of autologous origin. The adipose tissue fillant, in prolonged confinement and in the absence of infection, undergoes a liquefaction into its stable components of fatty acids and glycerol to yield a moderately viscous oil solution which serves as a lubricant to reduce the incidence of friction induced rupture. Upon implantation, the prosthesis presents a natural feeling to both the patient and to the touch.

The adipose tissue implant is radiolucent. Since the fat is confined within the envelope, it will not be subject to contact with fibroblasts which would otherwise cause fibrotic changes, calcification and appear in radiography procedures. However, invariably some micro-osmotic shift of the fatty acids is possible through a semipermeable silicone envelope. These liberated fatty acids will be metabolized by normal body function, or will contribute to the formation of a calcification layer on the outer surface of the envelope; a certain degree of calcification is found on virtually all envelopes regardless of fillant. In any event, the calcifications are readily identifiable in radiography procedures, such as mammographies.

The adipose tissue implant of the present invention yields substantially fewer incidences of fillant rejection, especially where autologous fat tissue is utilized. In the event of traumatic rupture, the body's normal immune system can metabolize and/or eliminate the adipose tissue components. Nevertheless, in this circumstance, removal of the fillant material from the body is advised. This can largely be accomplished by irrigation of the tissue at the same time as the envelope is removed.

The preferred method of the present invention involves the collection of fatty tissue, from fat sites of the patient receiving the implant using, known liposuction techniques. Either wet or dry liposuction techniques may be employed, although it has been the inventor's experience that use of the wet liposuction techniques yields more blood free fatty tissue. The collected fat is drained and rinsed, if necessary, to remove any excess blood and drained again. An appropriate amount of the cleansed fat is then measured and introduced into the internal cavity of a flexible envelope through a sealable valve. Thereafter, the prosthesis is implanted using known surgical techniques.

It is therefore an object of the present invention to provide an implantable prosthesis which overcomes the dangers and deficiencies of the prior implantable prosthesis, specifically saline and silicone filled implants.

It is a further object of the present invention to provide an implantable prosthesis having a fillant which is not harmful to the patient in the event of seepage or rupture.

It is a further object of the present invention to provide an implantable breast prosthesis that closely mirrors the natural feel of the human breast.

It is still a further object of the present invention to provide an implantable prosthesis which exhibits a markedly reduced incidence of fillant rejection compared to that of the prior art prosthesis.

These and other objects of the present invention will become more readily apparent from a reading of the detailed description taken in conjunction with the drawings.

DESCRIPTION OF THE DRAWINGS

FIG. 1 is a schematic view illustrating one method for extraction and collection of autologous adipose tissue for subsequent use as a prosthesis fillant;

FIG. 2 is schematic view illustrating one method for introducing adipose tissue fillant into a prosthesis envelope;

FIG. 3 is a front elevational view of the stopcock used in FIG. 2;

FIG. 4 is a front elevational view of one embodiment of a filling cannula for use introducing adipose tissue into a flexible prosthesis envelope.

DETAILED DESCRIPTION OF THE PREFERRED EMBODIMENT

The present invention discloses an implantable prosthesis for use in reconstructive or elective surgical tissue recontouring, most commonly mammoplasty. The device of the present invention is an implantable prosthesis comprising an impermeable or semi-permeable envelope containing adipose or fatty tissue.

Flexible envelopes for use as an implantable prosthetic shell with an internal cavity capable of retaining fillant material are known. Such envelopes typically utilize a valve for introducing fillant material into the cavity, each envelope capable of permanent or semi-permanent sealing. Flexible envelopes for use with the present invention are typically silicone-based envelopes, although polyurethane and other bio-compatible polymers possessing various degrees of elastic memory and permeability are contemplated.

The fillant material is primarily non-fibrous adipose tissue, preferably of human origin and most preferably autologous tissue collected during liposuction procedures. While it is preferred that autologous tissue harvested in an immediately preceding lipectomy procedure is utilized to reduce tissue rejection problems, it is contemplated that tissue preserved by cryogenics or other means may be utilized as well as cadaver or donor tissue. The fat or adipose tissue in the preferred method is harvested and collected through suction-assisted lipectomy procedures or liposuction and obtained from localized collections of excess fat, most commonly in the hips, thighs, buttocks and lower abdomen. As previously stated, wet or dry liposuction techniques can be employed for such collection, although the inventor has found that the current wet liposuction techniques yield a more blood free fat product for subsequent filling of a prosthesis. Practioners utilizing the wet liposuction technique employ numerous liposuction solutions. The inventor's preferred liposuction solution is as follows:

1000 iu Wydase™ (hyaluronidase)

60 cc 1% Lidocaine/Epinephrine (1:100,000)

100 cc Sterile Water 1000 cc Normal Saline

This solution is slightly hypotonic and mixes with the fat tissue as it is withdrawn.

The hyaluronidase is thought to promote diffusion of the solution into the extracted tissue through hydrolysis of hyaluronic acid of any fibrous tissue.

Since 400 cc's or more of pure fat volume are often needed in most procedures, such as breast augmentation, the use of a large, multi-opening cannula is preferred in order to simplify and maximize the overall fat collection. Consistent with known lipectomy procedures, a reservoir of fat is collected in a sterile suction canister. In the event insufficient fat is collected in this procedure, the fat fillant may be supplemented with normal saline or other essentially isotonic and tissue compatible liquid.

A currently preferred suction canister is illustrated in FIG. 1. Suction canister 10 is an essentially two compartmented container made of suitable plastic or glass, and most preferably capable of sterilization. The adipose tissue 20 is removed via lipectomy techniques using a cannula (not shown but described above), in communication with compartment A of suction canister 10 connected with surgical tubing of appropriate diameter. The suctioned adipose tissue 20' is retained within a cheese cloth strainer or equivalent, to permit drainage.

Suction is maintained using a vacuum inducing device 14, as is well known in the practice of lipectomy procedure, connected to compartment B of suction canister 10. Compartment A and compartment B of suction canister 10 are connected through an opening (not shown) in the lower portion of the common wall separating the two compartments.

An off-line suction unit 16 may be utilized to remove any liquid exudate 22 via valve 18 located near the bottom of canister 10.

Following cleansing and draining, as described supra, the adipose tissue 20' is transferred to a clean container 30. Here the adipose tissue 20' is withdrawn through surgical tubing into a calibrated syringe 32 using a three-way stopcock 34, shown in FIG. 3. The stopcock 34 is adapted to receive the syringe 32 at stopcock opening 35 using a friction fit. Currently a Toomey syringe is preferred.

After the calibrated volume of fat is withdrawn into syringe 32, a valve 36 of stopcock 34 is rotated to provide fluid communication exclusively between syringe 32 and a filler cannula 38 through an additional length of surgical tubing. Filler cannula 38, illustrated in FIG. 4, is preferably a single opening cannula having an approximately 3 mm diameter and a blunt end, so as not to puncture the flexible envelope 40.

In order to be suitable for use as a fillant, the fat should be as devoid of blood products as possible. To this end, single or multiple rinsing is advised. Currently, manual rinsing with a U-100 insulin-normal saline solution (1,000 U/500 cc) is preferred, although it is recognized that a multitude of alternative rinsing agents could be utilized. The wash solution is thoroughly drained from the fat reservoir.

Following the collection and cleansing steps, a predetermined quantity of fat is withdrawn from the reservoir using a calibrated syringe or similar device and at least a portion of this fat is subsequently injected into a selected flexible envelope of predetermined size. The implants typically contains at least 60 cc's of fat, with breast augmentation normally utilizing 200–1000 cc of fat per implant. However, the quantities are to in no way be seen as limiting. It is to be noted, but not required, that the inventor currently prefers selecting an envelope which has a capacity approximately 20 cc larger than the calculated volume of fat. It has been found that this slightly larger envelope reduces the pressure on the seams and valve of the envelope and further allows a better feel post-augmentation without a ballooning effect. In an alternative embodiment, the fat filled implant may be subjected to know sterilization steps or techniques prior to surgical insertion, to reduce the possibility of infection from contamination.

Incomplete filling of the envelope with the calculated volume of fat while the implant is external to the ultimate implant site permits easier implantation. In the case of mammoplasty, the partially filled implant is then inserted into the breast site and the balance of filling is accomplished with the implant situated within the implant site. The syringe or similar device is removed and the implant sealed. The filling and implanting procedure is repeated with the opposite breast.

In prolonged confinement and in the absence of infection, the adipose tissue fillant undergoes at least a partial liquefaction into its stable components of fatty acids and glycerol yielding a moderately viscous oil solution. A small amount of aqueous solution, resulting from irrigation and rinsing, may also be present.

In Magnetic Resonance Imaging (MRI) using a T-1 scan, the implant generates a magnetic signal intensity essentially equal to that of normal adipose breast tissue. Implants using homogenous oil solutions, generally generate a signal of approximately ten percent (10%) greater intensity than the normal breast tissue, which may distort or obscure the image of tissue immediately in front of or before this implant.

The maintenance of sterile conditions during the extraction, cleansing of the fat and the administration of a determined volume of fat into the implant is necessary to prevent the introduction of bacteria into the filled implant which could result in the necrosis of the fat fillant. As prophylaxis, antimicrobials are administered into the fat fillant. Currently the preferred antimicrobials include ciprofiloxacin or a mixture of clindamycin and vancomycin or tobramycin, although it is appreciated that countless antimicrobials, alone or in combination may be employed. Further ingredients such as anticoagulants, buffers or antioxidants are employed as needed to maintain the integrity of the fillant.

While in accordance with the patent statutes, a preferred embodiment and best mode have been presented, the scope of the invention is not limited thereto, but rather is measured by the scope of the attached claim.

What is claimed is:

1. An autologous implant prosthesis for insertion into a living being, comprising:
    a flexible envelope;
    a volume of mammalian adipose tissue obtained from said living being, said mammalian adipose tissue containing a high percentage of triglycerides, retained within said flexible envelope, said adipose tissue being incapable of vascularized contact with adjacent tissue upon insertion of said adipose-filled envelope into said living being from which the volume of adipose tissue was obtained.

2. The implant prosthesis as recited in claim 1 wherein said mammalian adipose tissue comprises fatty acids and glycerol.

3. The implant prosthesis as recited in claim 1 wherein said implant prosthesis further comprises an antimicrobial within said envelope.

4. The implant prosthesis as recited in claim 1 wherein said implant prosthesis further comprises one or more components from the group consisting of anticoagulants, buffers, and antioxidants.

5. The implant prosthesis as recited in claim 1 wherein said flexible envelope comprises one or more materials from the group of materials consisting of silicones, polyurethanes and bio-compatible polymers.

6. A method for producing an autologous implant prosthesis for subsequent insertion into a living being comprising the steps of:
    (a) obtaining a reservoir of substantially mammalian adipose tissue from a living being, said mammalian adipose tissue containing a high percentage of triglycerides;
    (b) introducing a determined volume of said adipose tissue from said reservoir into a flexible envelope of suitable material for use as a prosthetic shell;
    (c) sealing said flexible envelope containing said adipose tissue to create an implant prosthesis, said adipose tissue being incapable of vascularized contact with adjacent tissue upon insertion of said envelope into said human body; and
    (d) surgically implanting said implant prosthesis into said living being from which the reservoir of adipose tissue was obtained.

7. The method for producing an implant prosthesis as recited in claim 6 comprising the further step of, inserted following step (a) or (b):
    (e) cleansing said reservoir of said adipose tissue.

8. The method for producing an implant prosthesis as recited in claim 6 comprising the further step of, inserted following step (a) or (b):
    (f) adding one or more components from the group consisting of antimicrobials, anticoagulants, buffers, and antioxidants to said reservoir of adipose tissue.

9. The method for producing an implant prosthesis as recited in claim 6 wherein said adipose tissue comprises fatty acids and glycerol.

10. The method for producing an implant prosthesis as recited in claim 6 wherein said flexible envelope comprises one or more materials from the group of materials consisting of silicones, polyurethanes and bio-compatible polymers.

11. The method for producing an implant prosthesis as recited in claim 6 wherein said reservoir has a volume of at least 400 milliliters.

12. The method for producing an implant prosthesis as recited in claim 6 wherein said adipose tissue is a semi-solid.

13. The method for producing an autologous implant prosthesis for subsequent insertion into a living being comprising the steps of:
    (a) obtaining a reservoir of substantially mammalian adipose tissue from a living being, said mammalian adipose tissue containing a high percentage of triglycerides;
    (b) introducing at least a portion of a determined volume of said adipose tissue from said reservoir into a flexible envelope of suitable material for use as a prosthetic shell;
    (c) surgically implanting said flexible envelope containing at least a portion of said determined volume of said adipose tissue into said living being from which the reservoir of adipose tissue was obtained;
    (d) introducing a remainder of said determined volume of said adipose tissue into said flexible envelope;
    (e) sealing said flexible envelope containing said adipose tissue to create an implant prothesis, said adipose tissue being incapable of vascularized contact with adjacent tissue upon insertion of said envelope into said human body.

14. The method for producing an implant prosthesis as recited in claim 13 comprising the further step of, inserted following step (a) or (b):

(e) cleansing said reservoir of said adipose tissue.

15. The method for producing an implant prosthesis as recited in claim 13 comprising the further step of, inserted following step (a) or (b):

(f) adding one or more components from the group consisting of antimicrobials, anticoagulants, buffers, and antioxidants to said reservoir of adipose tissue.

16. The method for producing an implant prosthesis as recited in claim 13 wherein said adipose tissue comprises fatty acids and glycerol.

17. The method for producing an implant prosthesis as recited in claim 13 wherein said flexible envelope comprises one or more materials from the group of materials consisting of silicones, polyurethanes and bio-compatible polymers.

18. The method for producing an implant prosthesis as recited in claim 13 wherein said reservoir has a volume of at least 400 milliliters.

19. The method for producing an implant prosthesis as recited in claim 13 wherein said adipose tissue is a semi-solid.

* * * * *